United States Patent [19]
Vande Streek et al.

[11] Patent Number: 5,485,835
[45] Date of Patent: Jan. 23, 1996

[54] VENTILATION SYSTEM FOR DIAGNOSTIC IMAGING

[76] Inventors: Penny R. Vande Streek, 4259 Rawhide Rd., Rocklin, Calif. 95677; Tyrone Young, 6602 Munich Rd., San Antonio, Tex. 78256; Frederick L. Weiland, 4950 Keane Dr., Carmichael, Calif. 95608; Ronald Borchert, 5328 Boulware Ct., Charlotte, N.C. 28277

[21] Appl. No.: 323,082

[22] Filed: Oct. 14, 1994

[51] Int. Cl.⁶ .................................................. A61M 36/04
[52] U.S. Cl. ................. 128/205.13; 128/204.18; 128/203.12; 128/205.21
[58] Field of Search .............. 128/205.13, 204.18, 128/202.27, 203.12, 203.14, 203.21, 203.24, 203.28, 205.21, 911, 912

[56] References Cited

U.S. PATENT DOCUMENTS

| | | | |
|---|---|---|---|
| 3,848,773 | 11/1974 | Adler et al. | 222/5 |
| 4,088,131 | 5/1978 | Elam et al. | 128/205.13 |
| 4,094,317 | 6/1978 | Wasinch | 128/200.16 |
| 4,192,438 | 3/1980 | Foster et al. | 222/5 |
| 4,565,301 | 1/1986 | Hubbard et al. | 222/5 |
| 4,660,547 | 4/1987 | Kremer | 128/1.1 |
| 5,072,726 | 12/1991 | Mazloomdoost et al. | 128/203.12 |
| 5,099,833 | 3/1992 | Michaels | 128/200.14 |
| 5,181,508 | 1/1993 | Poole | 128/203.12 |

OTHER PUBLICATIONS

Samuel J. & Houlder A. E., *Clin Otolaryngol*, vol. 12, pp. 115–117, (1987).

*Primary Examiner*—Edgar S. Burr
*Assistant Examiner*—William J. Deane, Jr.
*Attorney, Agent, or Firm*—Gunn, Lee & Miller

[57] ABSTRACT

The present invention is directed a ventilation system used in the diagnostic imaging of a patient's pulmonary function, and more particularly, is directed to a disposable radioactive inhalation adaptor to be used in conjunction with standard ventilation apparatus. More specifically, the invention involves a hand-held ventilation system which delivers oxygen as well as the appropriate dose of Xenon-133 gas to the patient without contaminating the area. The claimed ventilation system is particularly designed for use with patients who cannot breathe on their own or who cannot cooperate with the standard respiratory diagnostic imaging apparatus.

22 Claims, 3 Drawing Sheets

VENTILATION SYSTEM FOR DIAGNOSTIC IMAGING

BACKGROUND OF THE INVENTION

1. Field of the Invention

The present invention relates generally to a ventilation system used in respiratory diagnostic imaging. Specifically, the present invention relates to devices used in the diagnostic imaging of a patient's pulmonary function, and more particularly, is directed to a disposable inhalation adaptor to be used in conjunction with standard, portable, ventilation apparatus. More specifically, the invention involves a hand-held ventilation system which delivers oxygen as well as the appropriate dose of Xenon-133 gas to the patient without contaminating the surrounding area. The claimed ventilation system is particularly designed for use with patients who cannot breathe on their own or who cannot cooperate with the standard respiratory diagnostic imaging apparatus.

2. Background Information

Performing ventilation imaging on a patient requires the patient to inhale radioactive material. The images of the distribution of the radioactive material provide a means for assessing the anatomy and physiology of the lung through diagnostic testing.

Respiratory diagnostic imaging is performed to determine the functioning; i.e., inhalation and exhalation capability, of the lungs of a patient. In assessing whether a patient's lungs are functioning, the physician first will order a regular chest X-ray which will provide an image of the anatomy of the lung of a particular patient. Then, the physician will order a radioactive ventilation scan and compare the X-ray and imaging of the lungs to determine which portions of the lungs are functioning and not functioning. The ventilation images are usually compared to radioactive perfusion images to assess blood flow in relation to ventilation: gas delivery and gas exchange.

Standard ventilation systems for respiratory diagnostic imaging have been developed and are presently used in patients who are able to cooperate with their use. These systems utilize a mask which straps onto the face of the patient covering the nose and mouth. The mask has one opening through which the Xenon-133 gas is introduced and through which the gas is exhausted into a radioactive trapping device. The patient inhales the Xenon-133 into the lungs and a gamma camera is used to take an image of the Xenon-133 which is present in the lungs.

There are, however, patients who require respiratory diagnostic imaging but who cannot be imaged using the standard ventilation systems. These patients include those who are unable to breath on their own and who are on ventilators or patients who can breath on their own but cannot cooperate with the standard ventilation imaging techniques, such as a pediatric patient or a sedated or comatose patient.

The ventilation system for respiratory diagnostic imaging of the present invention can be used on intubated patients by attachment to their tracheal tubes or can be used on patients who do not have tracheotomies but who cannot breathe on their own by attachment to a mask which covers the nose and mouth of the patient.

Additionally, the ventilation system of the present invention reduces the amount of "dead space" from the inhalation adaptor forward into the patient and the patient's airways. The "dead space" refers to the amount of space including either tubing or human airways which is not involved or participating in the actual exchange of oxygen with the blood. If the "dead space" is too large, then there is poor oxygenation of the patient and eventually respiratory compromise. At present, standard imaging systems have extensive tubing which results in large amounts of "dead space" providing unacceptable ventilation support. The present system overcomes these disadvantages of the standard imaging systems as a result of the use of a one-way valve in the present system which reduces the dead space.

Thus, a need exists for a ventilation system for diagnostic imaging which can be used to perform respiratory diagnostic imaging on patients who are on ventilators or who cannot cooperate with standard ventilation imaging techniques. Further, it is necessary that this apparatus provide an enclosed system to deliver radioactive gas and recover it after delivery without any contamination to the surrounding area and personnel performing the imaging.

SUMMARY OF THE INVENTION

It is an object of the present invention to provide a novel device to be used in the respiratory diagnostic imaging of a patient's pulmonary function.

It is another object of the present invention to provide a disposable inhalation adaptor to be used in conjunction to retrofit a standard hand-held ventilation apparatus for respiratory diagnostic imaging.

It is another object of the present invention to provide a hand-held ventilation imaging system which delivers oxygen as well as the appropriate dose of Xenon-133 gas to the patient without contaminating the surrounding area and personnel.

It is another object of the present invention to provide a method of using the hand-held ventilation imaging system of the present invention to deliver adequate oxygen by reducing the "dead space" in the system and to safely deliver a dose of Xenon-133 gas to the patient prior to the diagnostic imaging of the lungs of the patient.

In satisfaction of these and related objectives, the present invention provides a disposable inhalation adaptor to retrofit a known hand-held ventilation system and provides a disposable and portable ventilation system for respiratory diagnostic imaging of a patient population which previously could not be imaged using standard respiratory imaging apparatus. The diagnostic imaging ventilation system of the present invention also allows the radioactive gas used in the diagnostic imaging to be safely vented into a standard radioactive trapping member which is shielded for storage until the radioactivity in the gas has decayed for safe disposal.

More specifically the inhalation adaptor of the present invention contains a one-way valve which attaches to a known hand-held ventilation system and which can then be used to introduce radioactive gas; e.g., Xenon-133, as well as oxygen into a patient's lungs. The present invention also provides the complete hand-held ventilation imaging system for introducing oxygen and radioactive gas into a patient's lungs.

The apparatus of the present invention permits the diagnostic imaging of the lungs of patients who heretofore could not be evaluated for lung functionality because the standard ventilation systems for respiratory diagnostic imaging depended upon the patients' cooperation.

The present invention discloses an inhalation adaptor which can be retrofitted onto any standard hand-held ventilation bag providing a closed system, thus not venting radioactive gases into the room. Preferably, a hand-held ventilation bag known as a Jackson-Rees bag is used. The Jackson-Rees bag is composed of an inflatable rubber bag to which is attached a flexible tubing. This tubing is attached to a connector of the Jackson-Rees bag at the opposite end from the rubber bag, which also allows attachment to a connector port on the patient and also contains an inlet for a flexible tubing which attaches to an oxygen source. The Jackson-Rees bag is normally used to ventilate a patient who cannot breath on his own in instances when the patient is transported to and from areas in the hospital when he is off of his standard oxygen supply or a respirator.

In the present invention, the Jackson-Rees bag is modified by fitting the inhalation adaptor between the ventilation bag and its connector, which facilitates connection to the patient and which contains the oxygen inlet tubing. The adaptor allows the Jackson-Rees bag to be used to deliver radioactive gas as well as oxygen to the patient in an enclosed system thus avoiding radioactive contamination of the immediate area and to personnel performing the diagnostic imaging. Even though the Jackson-Rees bag is the preferred bag to be modified, any hand-held ventilation bag could be similarly adapted as long as the adaptor is connected to the bag tightly so that the radioactive gas cannot leak out of the system.

The present invention also discloses a complete ventilation system for diagnostic imaging which includes a modified Jackson-Rees bag containing the adaptor of the present invention.

The adaptor-fitted Jackson-Rees bag is used in the same manner as the unmodified Jackson-Rees bag to continue to ventilate the patient; however, as a result of the modification, the adaptor-fitted Jackson-Rees bag can now be used to deliver and recover radioactive gas for the purpose of performing respiratory diagnostic imaging.

DETAILED DESCRIPTION OF THE PREFERRED EMBODIMENT

Figure 1:
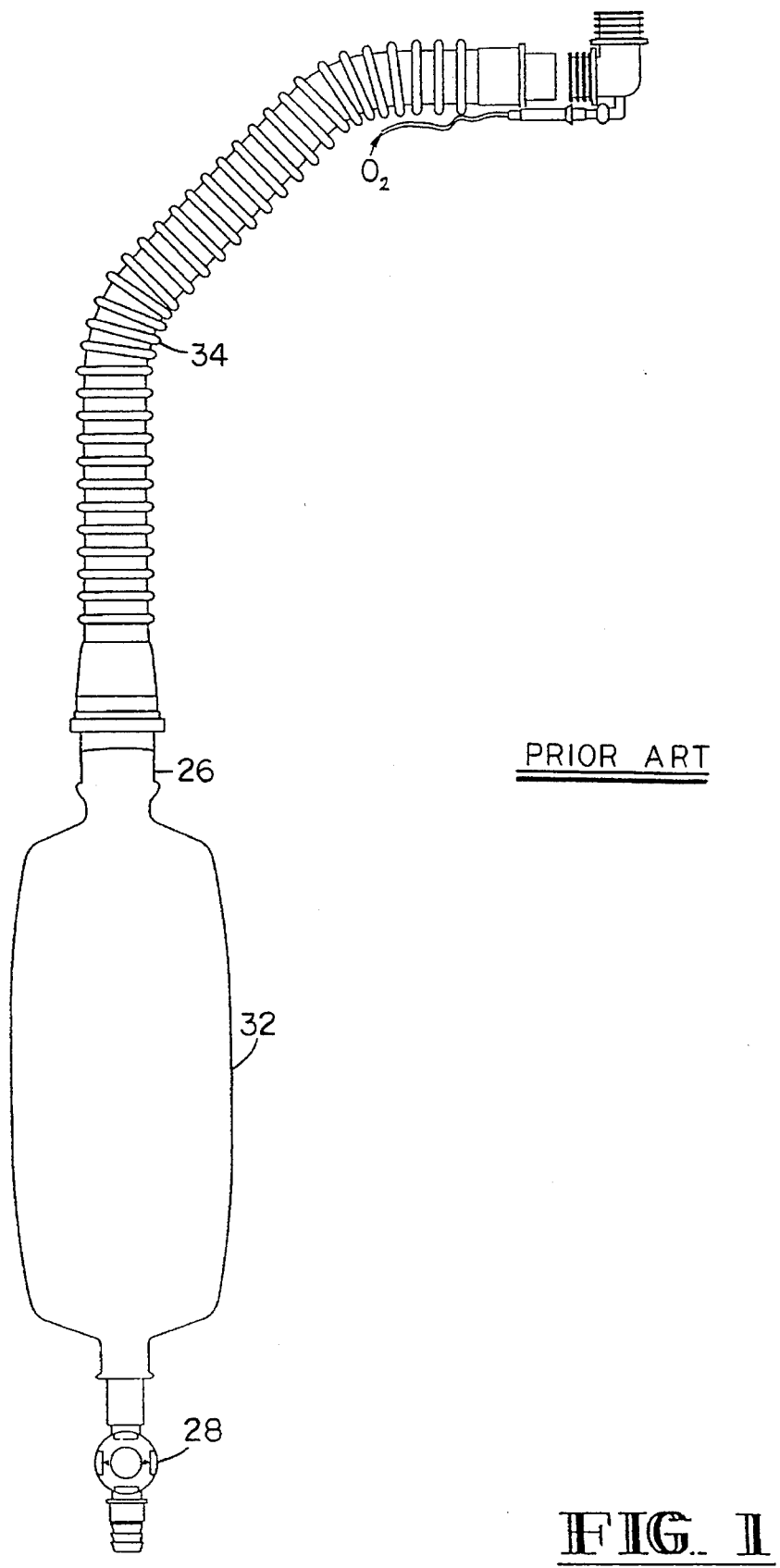
FIG. 1 is a perspective view of a prior art Jackson-Rees ventilation bag.

The prior art hand-held ventilation bag, the Jackson-Rees bag, is shown in FIG. 1. This bag is normally used to temporarily ventilate patients who need oxygen when they are transported within the hospital and away from the standard respiration equipment. The Jackson-Rees bag or any similar type ventilation bag has not heretofore been utilized as part of a radioactive respiratory diagnostic imaging system. The Jackson-Rees bag will be described in detail as it relates to the attachment of the inhalation adaptor (10) when detailed reference is made to FIG. 3.

Figure 2:
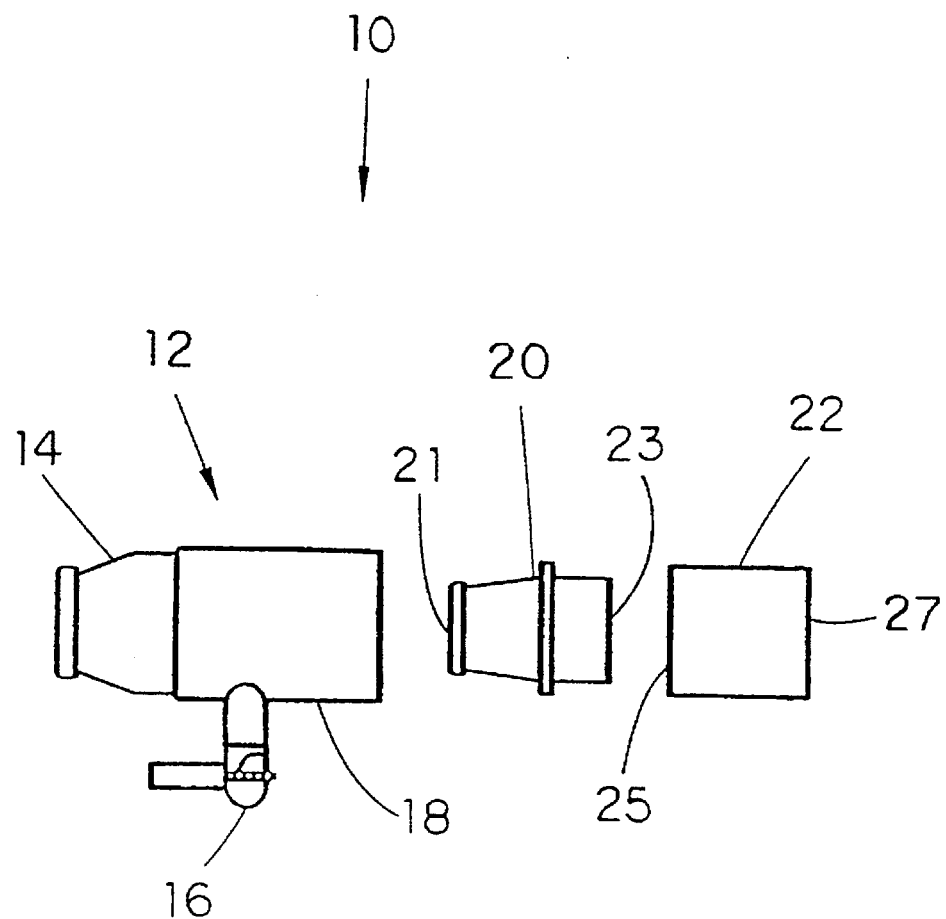
FIG. 2 is a perspective view of the inhalation adaptor of the present invention.

Reference is now made to FIG. 2 which is a perspective view of the inhalation adaptor (10) of the present invention which is used to modify a standard hand-held ventilation bag; e.g. a Jackson-Rees bag shown in FIG. 1. The adaptor (10) contains three components which are a three-legged connector (12), a one-way valve (20) and a dose chamber (22).

The three-legged connector (12) has three legs. The first leg (14) of the three-legged connector (12) is for attachment to a first flexible tubing which is part of the ventilation bag. The second leg (16) of the three-legged connector (12) is for attachment to a second flexible tubing which is attached to an oxygen source. The third leg (18) of the three-legged connector (12) is attached to the inlet end (21) of the one-way valve (20).

It should be understood that any connector with three legs, could be used in the present invention, such as other connectors with different configurations, such as a Y-connectors or T-connectors. When the disposable inhalation adaptor (10) is connected to a standard hand-held ventilation bag, the function of the three-legged connector (12) is to allow the oxygen to flow into the ventilation bag and then to allow the oxygen to be forced from the ventilation bag through the one-way valve (20) into the patient's airways and lungs. Thus, any configuration which would function in this manner is encompassed by this invention.

The one-way valve (20) has an inlet end (21) and an outlet end (23). It functions to connect the three-legged connector (12) and the dose chamber (22), as well as containing a one-way valve which is important in maintaining the integrity of the system to prevent the backwash of radioactive gas into the ventilation bag and possibly into the oxygen source as well as limiting the "dead space" in the ventilation imaging system.

The three-legged connector (12) and the one-way valve (20) can be made of a rigid material, such as metal, glass, rubber, or plastic; however, a rigid plastic, such as polypropylene, polyurethane, or plastics with comparable properties, are preferred because it is intended that the ventilation system of the present invention be disposable. These connectors (12) and (20) can be made of any material which will allow an airtight fit of the components of the adaptor (10) to each other and to the hand-held ventilation bag. The one-way valve is preferably plastic but the actual valve inside is made of a rubber composition held in place by plastic members. The rubber composition only allows the flow of gas in one direction and not in the other direction. The configuration of one-way valves are known by persons skilled in the respiratory art.

The inlet end (21) of the one-way valve (20) is attached to the third leg (18) of the three-legged connector (12). The outlet end (23) of the one-way valve (20) is attached to a dose chamber (22) which has a first end (25) and a second end (27). The dose chamber (22) is made of a composition having self-sealing properties which allows the radioactive gas to be injected by a needle into a side wall of the dose chamber (22) but which does not allow leakage of the radioactive gas after the needle is withdrawn. The self-sealing composition seals the injection hole after removal of the needle preventing the escape of the radioactive gas into the environment. The self-sealing composition is a rubber composition and preferably is a silicone rubber composition.

The second end (27) of the dose chamber (22) is an outlet from the adaptor (10), and in fact, is for attachment to the connector, which is part of the standard hand-held ventilation bag prior to modification. This connector of the prior art ventilation bag was a means for connection to the patient to deliver oxygen, and in the ventilation system of the present invention, is a means for delivering the radioactive gas, as well as oxygen to the lungs of the patient and for recovery of the gas after delivery and imaging.

Figure 3:
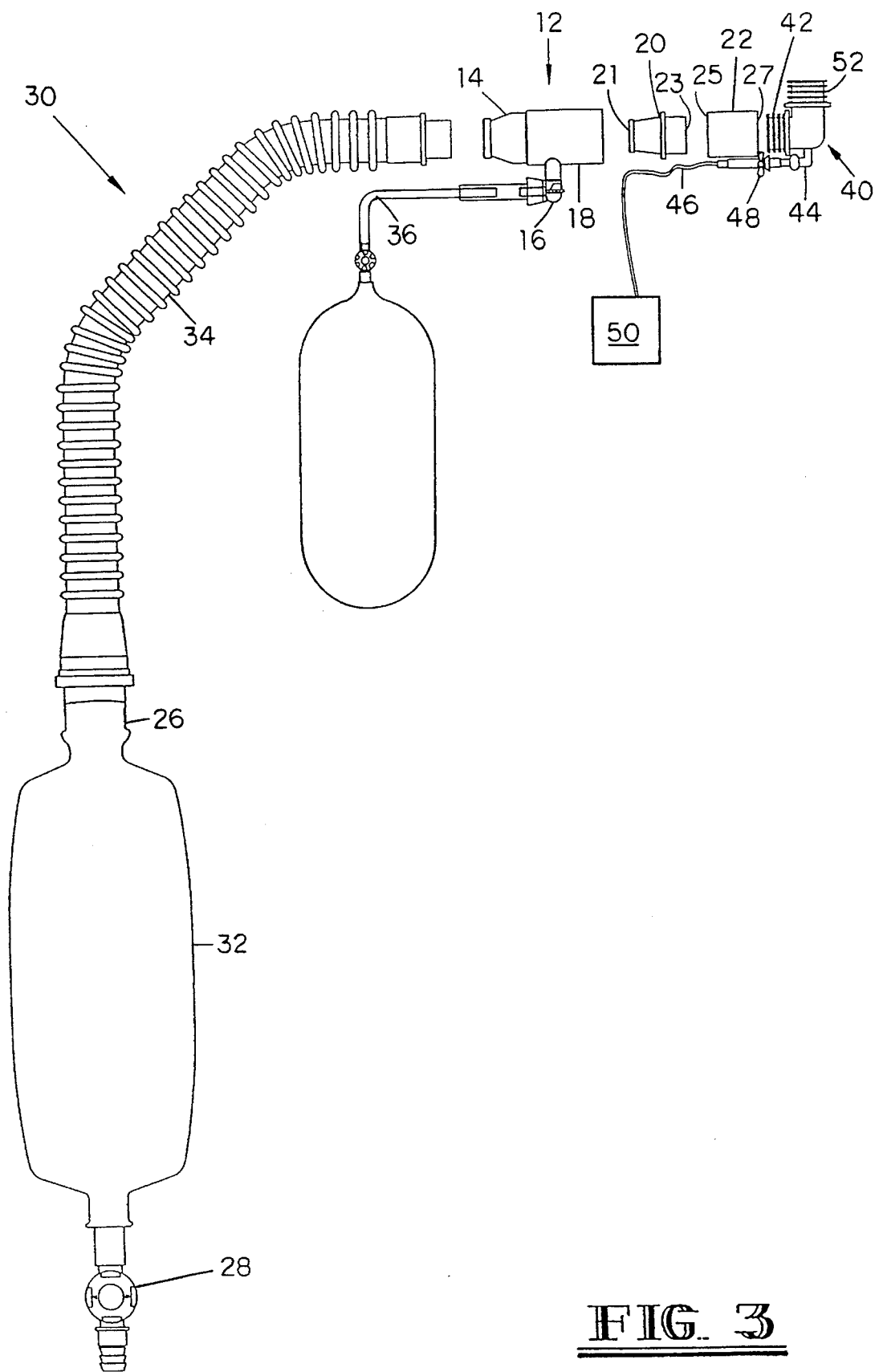
FIG. 3 is a perspective view of the complete ventilation system of the present invention.

Reference is now made to FIG. 3 which is a perspective view of the complete ventilation imaging system (30) of the present invention. The ventilation imaging system of the present invention is a modified standard hand-held ventilation bag which has been adapted to deliver radioactive gas and oxygen to the patient's lungs for diagnostic imaging.

The ventilation system (30) is comprised of a ventilation bag (32) which is closed at one end by a bleed-off valve on the back port (28) and which has a front port (26) to which is attached a first flexible tubing (34). The flexible tubing (34) is attached to the inhalation adaptor (10) at the first leg (14) of the three-legged connector (12). The second leg (16) of the three-legged connector (12) is for attachment to a second flexible tubing (36) which is attached to an oxygen source. The flow of oxygen through the second flexible tubing (36) into the ventilation bag (32) is controlled by adjusting the flow rate at the oxygen source. The third leg (18) of the three-legged connector (12) is attached to the inlet end (21) of the one-way valve (20).

The materials which the three-legged connector (12) and the one-way valve (20) can be made of have been discussed above. Additionally, different configurations of the three-legged connector, which could be used in the present invention, have also been discussed above. The function of the three-legged connector (12) is to allow the oxygen to flow into the ventilation bag (32) and then to allow the oxygen to be forced from the ventilation bag (32) through the one-way valve (20) into the patient's airways and lungs. Thus, any configuration which would function in this manner is encompassed by this invention.

As discussed above, the one-way valve (20) functions to connect the three-legged connector (12) to the dose chamber (22) as well as functioning as a one-way valve to prevent contaminating backwash of radioactive gas into the ventilation bag and possibly the oxygen source as well as limiting the "dead space".

The outlet end (23) of the one-way valve (20) is attached to a dose chamber (22). The dose chamber (22) has a first end (25) and a second end (27) and the one-way valve (20) is attached to the first end (25). The composition of the dose chamber (22) has also been discussed above. The self-sealing composition of the dose .chamber (22) seals the injection hole after removal of the needle which has been used to inject the radioactive gas into the ventilation system. The self-sealing composition is preferably a silicone rubber composition.

The second end (27) of the dose chamber (22) is attached to a patient connector (40) which is part of the standard hand-held ventilation bag prior to modification but in its adapted function is a means for delivering the radioactive gas to the lungs of the patient and for recovery of the gas after delivery and imaging.

The patient connector (40) has a first means (42) which is attached to the second end (27) of the dose chamber (22) and which allows the flow of oxygen and radioactive gas from the inhalation adaptor (10) attached to the ventilation bag into the patient's lungs,. The second means (44) of the patient connector (40) is for attachment to a third flexible tubing (46) which allows the radioactive gas to flow through it and be recovered in a radioactive gas trapping member (50) after delivery and washout from the lungs of the patient. The third means (52) of the patient connector (40) is for attachment to the patient via a patient connector port.

It is important that the diameter of the third flexible tubing (46) is of a sufficient diameter so as to lower air resistance, to make breathing easier for the patient, and to decrease the risk of barotrauma to the lungs during the washout from the lungs of the patient with the continued flow of oxygen into the lungs. Any flexible, non-porous tubing can be used; however, a medical grade tubing, such as TYGON tubing, or the equivalent is preferred and are well known by persons skilled in the art. The tubing should have a minimum inside diameter of approximately ¼ inch and an outside diameter of approximately ⅜ inch. However, the dimensions of the inside diameter must be sufficient to not place the patient in respiratory compromise from poor ventilation yet provide a tight fit to the second means (44) of the patient connector (40).

The flow of radioactive gas and oxygen through the third flexible tubing (46) is controlled by a gas flow control means (48). This gas flow control means (48) is preferably a stop cock twist valve with a single rotating part which has a hole to allow passage of gas through the flexible tubing (46) when the gas flow control means (48) is in an open position. This control means (48) can also be a valve, clip or any other means for controlling the flow of gas out of the ventilation system into the radioactive gas trapping member (50). The control means (48) should be located as close to the second means (44) as possible to minimize "dead space" and should not be greater than 3 cms away from the second means (44) along the portion of the flexible tubing (46).

The radioactive gas trapping member (50) is a system utilized in conjunction with routine ventilation imaging and is well known to persons skilled in the art. In a particular embodiment, the system allows the passage of the Xenon-133 into a jar which contains $CO_2$ crystals that absorb Xenon-133.

The preferred radioactive gas for use with the ventilation imaging system of the present invention is Xenon-133, although any radioactive gas which can appropriately be used to image lungs could be used with the present ventilation imaging system. Such appropriate radioactive gases can be determined by persons skilled in the art for use in the present system. For example, Krypton-81 m could be used in place of Xenon-133; however, its half-life is extremely short.

The purpose of the ventilation system of the present invention is to safely deliver radioactive gas, such as Xenon-133, as well as oxygen to the lungs of a patient who cannot breathe unassisted or who cannot cooperate with the standard diagnostic imaging apparatus so that the patient's lungs can be imaged and the functionality assessed. If the patient has a tracheotomy, the ventilation system via the third means (52) of the patient connector (40) will be attached directly to a patient connector or tube in the tracheotomy. If the patient does not have a tracheotomy, the ventilation system via the third means (52) will be attached directly to a patient connector port on an airtight mask placed over the nose and mouth of the patient.

For increased safety reasons, it is preferred that the system be adjusted for appropriate ventilation bag filling and oxygen flow for the individual patient prior to administration of the radioactive dose, as the opening of a bag port after the injection of Xenon-133 could allow the possibility of the efflux of Xenon-133. The flow rate of oxygen should be adjusted to approximately 3–4 liters/minute for pediatric patients and approximately 4–6 liters/minute for adults to maintain adequate ventilation bag filling without over extension of the bag. The timing of the dose delivery and washout must be coordinated with the individual ventilating the patient.

The ventilation imaging system of the present invention is used in the following way to deliver radioactive gas to the lungs of a patient for the purpose of diagnostic imaging:

Step 1— attaching a diagnostic imaging ventilation system (30) to a patient via a patient connector port, where the ventilation system comprises: a ventilation bag (32) having a first flexible tubing (34); a three-legged connector (12) having a first leg (14) attached to the first flexible tubing (34) of the: ventilation bag (32), a second leg (16) attached to a second flexible tubing (36) connected to an oxygen source and a third leg (18); a one-way valve (20) having an inlet end (21) and an outlet end (23), where the inlet end (21) of the one-way valve (20) is attached to the third leg (18) of the three-legged connector (12); a dose chamber (22) having a first end (25) and a second end (27), where the first end (25) of the dose chamber (22) is attached to the outlet end (23) of the one-way valve (20), the dose chamber (22) being made of a composition having self-sealing properties; and a patient connector (40) having a first means (42) attached to the second end (27) of the dose chamber (22), a second means (44) attached to a third flexible tubing (46), the tubing (46) containing a gas flow control means (48) for controlling the flow of the radioactive gas out of the ventilation system (30) and a third means (52) for attachment to a patient connector port;

Step 2— closing the gas flow control means (48) on the third flexible tubing (46);

Step 3— providing oxygen from the oxygen source and adjusting the flow of oxygen into the ventilation bag (32) to provide sufficient oxygen to the patient when deflating the ventilation bag (32) and forcing oxygen to flow into the lungs of the patient;

Step 4— injecting the radioactive gas through a side wall of the dose chamber (22);

Step 5— deflating the ventilation bag (32) and forcing the oxygen and the radioactive gas to flow through the ventilation system (30) and into the lungs of the patient;

Step 6— imaging the lungs of the patient with an apparatus, such as a gamma camera, which can detect the presence of the radioactive gas in the lungs of the patient;

Step 7— opening the gas flow control means (48) in the third flexible tubing (46); and Step 8— repeatedly deflating the ventilation bag (32) forcing the oxygen to flow through the ventilation system (30) into the lungs of the patient for a sufficient number of times to force the radioactive gas out of the lungs of the patient and through the third flexible tubing (46) into a radioactive gas trapping (50) member.

The preferred radioactive gas is Xenon-133 which is injected through the wall into the dose chamber (22). With the deflation of the ventilation bag (32) which has been filled with oxygen, oxygen is propel led through the ventilation system (30). The oxygen and Xenon-133 move forward out of the ventilation system (30) and are delivered into the patient's airways and lungs. The third flexible tubing (46) is closed prior to providing oxygen to the patient and prior to the injection of the Xenon-133 into the wall of the dose chamber (22) by closing the gas flow control means (48) and is opened following the diagnostic imaging. The Xenon-133 is washed out of the lungs and into the third flexible tubing (46) with the continued ventilation of the patient by deflating the constantly oxygen filled ventilation bag (32). The Xenon-133 is unable to pass into the ventilation system Back beyond the one-way valve (20) and must flow through the third flexible tubing (46) to the gas trapping member (50) located within a shielded housing of a standard ventilation system.

The ventilation system is disposable once the system has been appropriately stored for decay of the radioactive gas. This apparatus was designed to use the standard ventilation system trap for the exhaust of the Xenon-133 to decrease the cost of the system and waste.

At least 13 subjects to date have had their lungs imaged using the ventilation imaging system of the present invention. The results obtained by the diagnostic imaging provided by the use of this ventilation system were good and allowed the physician to assess the functioning of the patient's lungs. The method of respiratory diagnostic imaging of the present invention did not result in any complications to the subjects who were imaged nor did the ventilation system place the hospital staff at risk by exposure to radioactive gas leaking from the ventilation imaging system of the present invention.

The method of the present invention can be performed with a ventilation imaging system assembled by hospital staff where the inhalation adaptor (10) as shown in FIG. 2 is attached to a prior art hand-held bag, such as the Jackson-Rees bag as shown in FIG. 1. Alternatively, the method of the present invention can be performed with a ventilation imaging system (30) as shown in FIG. 3, completely pre-assembled and containing a hand-held ventilation bag, such as the Jackson-Rees bag, modified by the attachment of the inhalation adaptor (10) of the present invention. Further, the ventilation imaging system of the present invention could contain the second flexible tubing (36) and the third flexible tubing (46) already attached to the apparatus or the ventilation imaging system of the present invention could not contain these flexible tubings (35) and (46). Hospital staff could readily attach such tubings to fit the ventilation system (30) prior to use.

Although the invention has been described with relation to specific preferred embodiments which are set forth in detail, it should be understood that this is by way of illustration only and the invention is not necessarily so limited, since other embodiments or systems which would deliver radioactive gas to the lungs of patients who cannot cooperate with standard diagnostic imaging ventilation systems would be apparent to those skilled in the art in view of the disclosure of the present invention.

I claim:

1. An adaptor for attachment to a ventilation bag for delivering radioactive gas and oxygen to the lungs of a patient for the purpose of diagnostic imaging and for recovering said gas, wherein said adaptor comprises:

a three-legged connector having a first leg for attachment to a first flexible tubing of a ventilation bag, a second leg for attachment to a second flexible tubing connected to an oxygen source and a third leg;

a one-way valve having an inlet end and an outlet end, wherein said inlet end of said one-way valve is attached to said third leg of said three-legged connector; and a dose chamber having a first end and a second end, wherein said first end of said dose chamber is attached to said outlet end of said one-way valve and said second end of said dose chamber is an outlet from said adaptor, said dose chamber being made of a composition having self-sealing properties.

2. The adaptor of claim 1, wherein said three-legged connector and said one-way valve are made of a plastic composition.

3. The adaptor of claim 1, wherein said composition of said dose chamber is a rubber composition.

4. The adaptor of claim 3, wherein said rubber composition is silicone rubber.

5. A diagnostic imaging ventilation system for delivering radioactive gas and oxygen to the lungs of a patient for the purpose of diagnostic imaging and for recovering said gas, wherein said ventilation system comprises:

a ventilation bag having a first flexible tubing;

a three-legged connector having a first leg attached to said first flexible tubing of said ventilation bag, a second leg for attachment to a second flexible tubing connected to an oxygen source and a third leg;

a one-way valve having an inlet end and an outlet end, wherein said inlet end of said one-way valve is attached to said third leg of said three-legged connector;

a dose chamber having a first end and a second end, wherein said first end of said dose chamber is attached to said outlet end of said one-way valve, said dose chamber being made of a composition having self-sealing properties; and a patient connector having a first means attached to said second end of said dose chamber, a second means for attachment to a third flexible tubing and a third means for attachment to a patient connector port.

6. The ventilation system of claim 5, wherein said ventilation bag is a Jackson-Rees bag.

7. The ventilation system of claim 5, wherein said three-legged connector, said one-way valve, and said patient connector are made of a plastic composition.

8. The ventilation system of claim 5, wherein said composition of said dose chamber is a rubber composition.

9. The ventilation system of claim 8, wherein said rubber composition is silicone rubber.

10. The ventilation system of claim 5 wherein said first, said second and said third flexible tubings are made of a plastic composition.

11. The ventilation system of claim 5, wherein said second flexible tubing is attached to said second leg of said three-legged connector.

12. The ventilation system of claim 5, wherein said third flexible tubing is attached to said second means of said patient connector and wherein said third flexible tubing contains a gas flow control means for controlling the flow of said radioactive gas out of said ventilation system.

13. The ventilation system of claim 12, wherein said gas flow control means is a valve or a clip.

14. A method of delivering radioactive gas and oxygen to the lungs of a patient for the purpose of performing diagnostic imaging on said lungs and recovering said gas, wherein said method comprises:

attaching a diagnostic imaging ventilation system to a patient via a patient connector port, wherein said ventilation system comprises:

a ventilation bag having a first flexible tubing;

a three-legged connector having a first leg attached to said first flexible tubing of said ventilation bag, a second leg attached to a secord flexible tubing connected to an oxygen source and a third leg;

a one-way valve having an inlet end and an outlet end, wherein said inlet end of said one-way valve is attached to said third leg of said three-legged connector;

a dose chamber having a first end and a second end, wherein said first end of said dose chamber is attached to said outlet end of said one-way valve, said dose chamber being made of a composition having self-sealing properties; and a patient connector having a first means attached to said second end of said dose chamber, a second means attached to a third flexible tubing, said tubing containing a gas flow control means for controlling the flow of said radioactive gas out of said ventilation system and a third means for attachment to said patient connector port;

closing said gas flow control means on said third flexible tubing;

providing oxygen from said oxygen source and adjusting the flow of oxygen through into said ventilation bag to provide sufficient oxygen to said patient when deflating said ventilation bag;

injecting said radioactive gas through a side wall of said dose chamber;

deflating said ventilation bag and forcing said oxygen and said radioactive gas to flow through said ventilation system and into said lungs of said patient;

imaging said lungs of said patient with an apparatus which can detect the presence of said radioactive gas in said lungs of said patient;

opening said gas flow control means in said third flexible tubing; and repeatedly deflating said ventilation bag forcing said oxygen to flow through said ventilation system into said lungs of said patient for a sufficient number of times to force said radioactive gas out of said lungs of said patient and through said third flexible tubing into a radioactive gas trapping member.

15. The method of claim 14, wherein said ventilation bag is a Jackson-Rees bag.

16. The method of claim 14, wherein said three-legged connector, said one-way valve, and said patient connector are made of a plastic composition.

17. The methyl of claim 14, wherein said composition of said dose chamber is a rubber composition.

18. The method of claim 17, wherein said rubber composition is silicon rubber.

19. The method of claim 14, wherein said first, said second and said third flexible tubings are made of a plastic composition.

20. The method of claim 14, wherein said gas flow control means for controlling the flow of gas out of said third flexible tubing is a valve or a clip.

21. The method of claim 14, wherein said radioactive gas is Xenon-133.

22. The method of claim 14, wherein said patient connector port is present on a tracheal tube or on an airtight mask located on said patient.

* * * * *